(12) United States Patent
Wittenberger

(10) Patent No.: US 9,743,972 B2
(45) Date of Patent: Aug. 29, 2017

(54) CARDIAC CRYOLIPOLYSIS FOR THE TREATMENT OF CARDIAC ARRHYTHMIA

(71) Applicant: Medtronic CryoCath LP, Toronto (CA)

(72) Inventor: Dan Wittenberger, L'lle Bizard (CA)

(73) Assignee: Medtronic CryoCath LP, Toronto, Ontario (CA)

( * ) Notice: Subject to any disclaimer, the term of this patent is extended or adjusted under 35 U.S.C. 154(b) by 380 days.

(21) Appl. No.: 14/334,874

(22) Filed: Jul. 18, 2014

(65) Prior Publication Data
US 2016/0015444 A1    Jan. 21, 2016

(51) Int. Cl.
*A61B 18/20* (2006.01)
*A61B 18/02* (2006.01)
*A61B 18/00* (2006.01)

(52) U.S. Cl.
CPC ...... *A61B 18/02* (2013.01); *A61B 2018/0025* (2013.01); *A61B 2018/00351* (2013.01);
(Continued)

(58) Field of Classification Search
CPC .......... A61B 18/02; A61B 2018/00577; A61B 2018/00351; A61B 2018/0262; A61B 2018/0212; A61B 2018/0025
See application file for complete search history.

(56) References Cited

U.S. PATENT DOCUMENTS 5,972,013 A   10/1999  Schmidt
6,237,605 B1 *  5/2001  Vaska .................... A61B 18/02
                                                                   128/898
(Continued)

FOREIGN PATENT DOCUMENTS

ES       2267396 A1    3/2007
WO    2005112812 A1   12/2005
(Continued)

OTHER PUBLICATIONS

M. Obadah Al Chekakie, MD et al., Pericardial Fat Is Independently Associated with Human Atrial Fibrillation, Journal of the American College of Cardiology, vol. 56, No. 10, 2010, 5 pages.
(Continued)

*Primary Examiner* — Michael Peffley
(74) *Attorney, Agent, or Firm* — Christopher & Weisberg, P.A.

(57) ABSTRACT

A system, device, and method for the treatment of cardiac arrhythmia by, specifically, cryolipolysis of non-myocardial tissue and cryoablation of myocardial tissue. A system for treating cardiac arrhythmia may include a first thermal treatment device configured for placement within a heart in contact with myocardial tissue, a second thermal treatment device configured for placement in contact with pericardial tissue, an ablation energy source in communication with the first thermal treatment device, and a cooling energy source in communication with the second thermal treatment device, the cooling energy source causing the second thermal treatment device to reach a temperature insufficient for myocardial ablation when the second thermal treatment device is activated. A method of treating cardiac arrhythmia may include introducing a cooling element into a pericardial space proximate pericardial adipose tissue, and activating the cooling element to reduce the temperature of adjacent pericardial adipose tissue to approximately 0° C.

25 Claims, 7 Drawing Sheets

(52) U.S. Cl.
CPC ............... *A61B 2018/00577* (2013.01); *A61B 2018/0212* (2013.01); *A61B 2018/0262* (2013.01)

(56) References Cited

U.S. PATENT DOCUMENTS

| | | | |
|---|---|---|---|
| 6,805,128 B1 | 10/2004 | Pless et al. | |
| 8,057,465 B2 | 11/2011 | Sliwa, Jr. et al. | |
| 2005/0080469 A1 | 4/2005 | Larson et al. | |
| 2005/0182393 A1* | 8/2005 | Abboud | A61B 18/02 606/20 |
| 2005/0187545 A1* | 8/2005 | Hooven | A61B 18/14 606/41 |
| 2006/0069385 A1* | 3/2006 | Lafontaine | A61B 18/02 606/21 |
| 2007/0149967 A1* | 6/2007 | Chapelon | A61B 18/1492 606/41 |
| 2007/0156185 A1 | 7/2007 | Swanson et al. | |
| 2009/0287202 A1 | 11/2009 | Ingle et al. | |
| 2010/0004661 A1* | 1/2010 | Verin | A61B 5/4233 606/129 |
| 2011/0060331 A1 | 3/2011 | Ibrahim et al. | |
| 2013/0190744 A1* | 7/2013 | Avram | A61F 7/10 606/21 |

FOREIGN PATENT DOCUMENTS

| | | |
|---|---|---|
| WO | 2007010073 A2 | 1/2007 |
| WO | 2007109171 A2 | 9/2007 |
| WO | 2009124220 A2 | 10/2009 |
| WO | 2012119088 A1 | 9/2012 |

OTHER PUBLICATIONS

Dieter Manstein et al., Selective Cryolysis: A Novel Method of Non-Invasive Fat Removal, Lasers in Surgery and Medicine 40:595-604 (2008).

International Search Report and Written Opinion dated Aug. 31, 2015, for corresponding International Application No. PCT/CA2015/000381; International Filing Date: Jun. 15, 2015 consisting of 10 pages.

Omar Batal, et al., Left Atrial Epicardial Adiposity and Atrial Fibrillation, Circulation Arrhythmia and Electrophysiology 2010;3:230-236.

Myung-Jin Cha, MD., The Relationship Between Pericardial Fat and Atrial Fibrillation, www.jafib.com, Feb.-Mar. 2013, vol. 5, Issue 5.

Tomasz Mazurek, MD. et al., Human Epicardial Adipose Tissue Is a Source of Inflammatory Mediators, Circulation 2003; 108: 2460-2466.

* cited by examiner

CARDIAC CRYOLIPOLYSIS FOR THE TREATMENT OF CARDIAC ARRHYTHMIA

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to a system, device, and method for the treatment of cardiac arrhythmia by, specifically, cryolipolysis of non-myocardial tissue and cryoablation of myocardial tissue.

BACKGROUND OF THE INVENTION

The development of effective treatments for cardiac arrhythmia, including atrial fibrillation, is of great concern. Adipose pericardial tissue volume was recently found to be independently correlated with several heart ailments, including atrial fibrillation. Although the exact mechanism behind this is still being elucidated, there are several findings that point to the deleterious role of the pericardial fat.

It has been demonstrated that the fatty tissue in the pericardial space is actively releasing pro-inflammatory cytokines. The pericardial fat is directly in contact with the myocardium. As such, it represents a pro-inflammatory entity, causing chronic inflammation of the myocardium in contact with it. Several sources describe a positive correlation between the level of inflammation markers in biopsy samples of atrial tissue from surgery patients and the magnitude of their pericardial adipose deposits. Additionally, the amount of pericardial adipose tissue may be related to the occurrence of cardiac arrhythmia, such as atrial fibrillation. The fact that most of the triggers causing paroxysmal atrial fibrillation originate from the pulmonary veins or the area immediately surrounding them, and the fact that these areas also coincide with adipose deposits, further underscores the link between the presence of pericardial fat and atrial fibrillation.

Recently, moderately cold temperatures were proposed as a means to reduce subcutaneous fatty deposits. For example, it has been demonstrated that applying temperatures slightly below 0° C. to the skin for several minutes results in a significant reduction of the fat layer occurring over a few weeks. The mechanism that makes adipose tissue more susceptible to cold-induced injury likely is linked to the higher crystallization temperature of cytoplasmic lipids in adipocytes, compared with the freezing temperature of water in myocites and other collateral tissues. The initially cold-induced injury in adipose cells likely leads to apoptosis. The process continues with cell removal by phagocytosis, such as by activated macrophages.

Therefore, it is desired to provide a system, device, and method for treating cardiac arrhythmia by causing lipolysis within pericardial adipose tissue either alone or in conjunction with the ablation of myocardial tissue within the heart.

SUMMARY OF THE INVENTION

The present invention advantageously provides a system, device, and method for the treatment of cardiac arrhythmia by, specifically, cryolipolysis of non-myocardial tissue and cryoablation of myocardial tissue. A system for treating cardiac arrhythmia may include a first thermal treatment device configured for placement within a mammalian heart in contact with myocardial tissue, a second thermal treatment device configured for placement in contact with pericardial tissue, an ablation energy source in communication with the first thermal treatment device, and a cooling energy source in communication with the second thermal treatment device, the cooling energy source causing the second thermal treatment device to reach a temperature that is insufficient for myocardial ablation when the second thermal treatment device is activated. The first thermal treatment device may be an ablation device, such as a cryoablation device including an elongate body and a cryoballoon coupled to a distal portion of the elongate body. The cryoballoon may be in fluid communication with the ablation energy source, such as a coolant source containing a cryogenic fluid. Cryogenic fluid may be circulated within the cryoballoon when the cryoablation device is activated, and activation of the cryoablation device may lower the temperature of the cryoballoon, causing the cryoballoon to ablate adjacent myocardial tissue. The second thermal treatment device may be a cooling device including an elongate body and a balloon coupled to a distal portion of the elongate body. The cooling energy source may be a coolant source containing a cryogenic fluid and/or a non-cryogenic fluid. The cryogenic fluid and/or the non-cryogenic fluid may be circulated within the balloon of the cooling device when the cooling device is activated, activation of the cooling device causing a reduction in the temperature of the balloon for at least one period of time to a temperature that is sufficient to cause cryolipolysis of adjacent pericardial tissue, for example, pericardial adipose tissue. Activation of the cooling device may cause a reduction in a temperature of adjacent pericardial tissue to approximately 0° C., and cooling of this adjacent pericardial tissue may be maintained for between approximately two minutes and approximately five minutes during each of the at least one period of time.

A system for treating cardiac arrhythmia may include: an ablation device including an elongate body and an ablation element coupled to the elongate body, the ablation device being configured for placement within a mammalian heart in contact with myocardial tissue; a cooling device including an elongate body and a cooling element coupled to the elongate body, the cooling device being configured for placement in a pericardial space in contact with pericardial adipose tissue proximate the ablation element; an ablation energy source in communication with the ablation element, the ablation energy source causing the ablation element to reach a temperature that is sufficient for myocardial ablation when the ablation element is activated; and a cooling energy source in communication with the cooling element, the cooling energy source causing the cooling element to reach a temperature that is insufficient for myocardial ablation when the cooling element is activated. The ablation element and the cooling element may be activated at the same time. Activation of the cooling element causes a reduction in temperature of adjacent pericardial adipose tissue to approximately 0° C., and this cooling may be maintained for at least one period of time, each of the at least one period of time being between approximately two minutes and approximately five minutes. Activation of the cooling element for a first period of time may cause a reduction in pericardial adipose tissue over a second period of time, and the second period of time may be greater than the first period of time.

A method of treating cardiac arrhythmia may include introducing a cooling element into a pericardial space within a patient's body, proximate pericardial adipose tissue, and activating the cooling element to reduce the temperature of adjacent pericardial adipose tissue to approximately 0° C. for a period of time. For example, the temperature of the adjacent pericardial adipose tissue may be reduced to approximately 0° C. for a first period of time and the temperature reduction causes a removal of the pericardial adipose tissue over a second period of time, the second period of time being greater than the first period of time. The method may further include introducing an ablation element into the patient's heart, proximate myocardial tissue, and activating the ablation element to ablate adjacent myocardial tissue. The ablation element and the cooling element are activated simultaneously. The cooling element may be in communication with a source of cooling energy and the ablation element is in communication with a source of ablation energy. The source of cooling energy and the source of ablation energy may be the same or different. For example, the source of cooling energy may be a non-cryogenic fluid and the source of ablation energy may be a cryogenic fluid.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
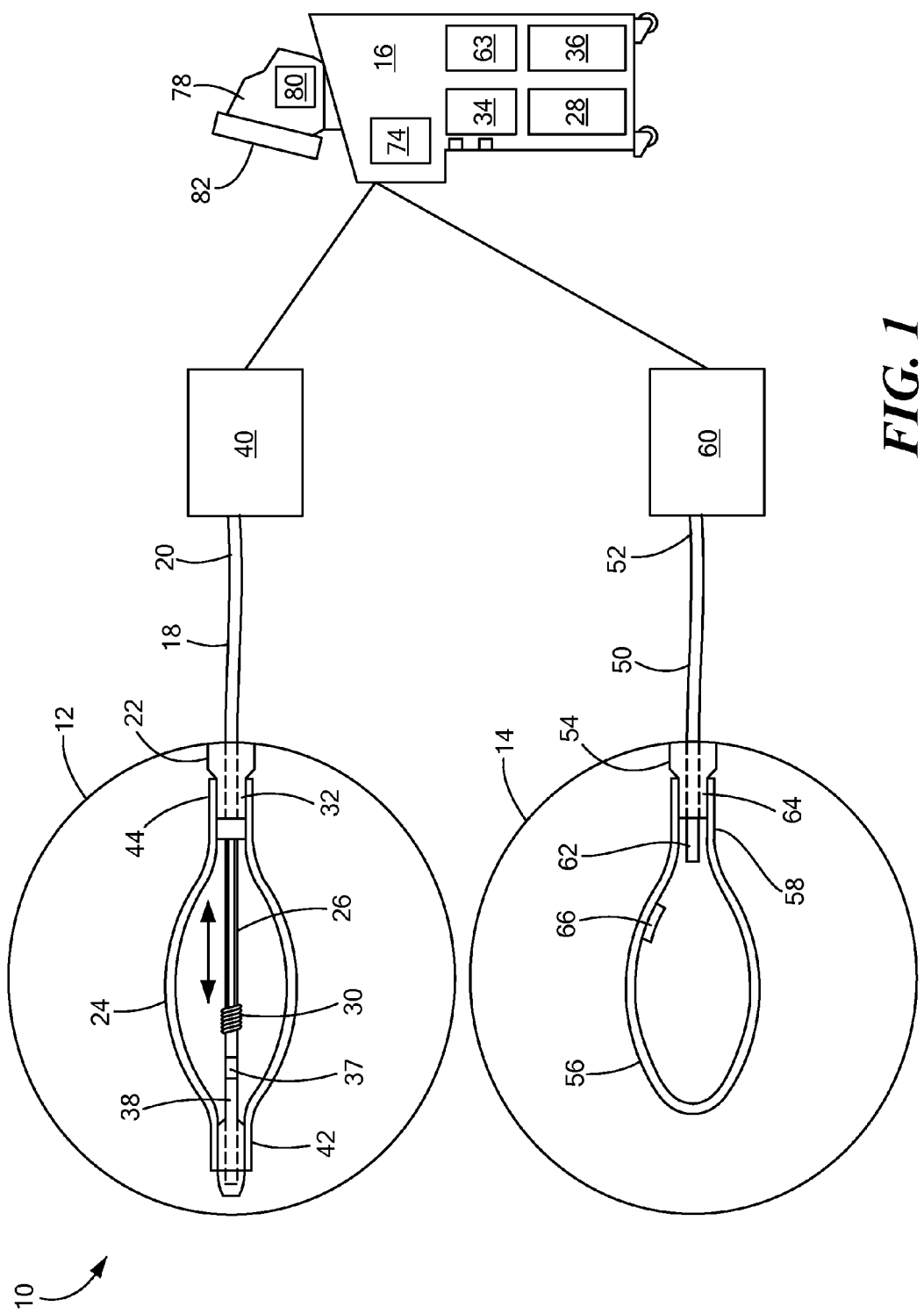
FIG. 1 shows an exemplary system for the treatment of cardiac arrhythmia in accordance with the present invention.

Referring now to FIG. 1, an exemplary system for the treatment of atrial fibrillation is shown. In general, the system 10 may include a first thermal treatment device 12, a second thermal treatment device 14, and a control unit 16. The first thermal treatment device 12 may be an ablation device that is configured to treat a variety of cardiac surfaces, including the tissue surrounding the pulmonary veins. For example, the ablation device may include an elongate body 18 having a proximal portion 20, a distal portion 22, and one or more lumens therebetween. The ablation device may be in contact with an ablation energy source and adapted for use with any of a variety of ablation modalities, including cryoablation, radiofrequency ablation, laser ablation, ultrasound ablation, and/or hot balloon ablation. If the ablation device 12 is used to ablate tissue using cryoablation, the device 12 may include an expandable element, such as a balloon 24, coupled to the distal portion 22 of the elongate body. Further, the elongate body 18 may include a coolant delivery conduit 26 for delivering coolant from the ablation energy source, for example, a coolant source 28 containing a cryogenic fluid, to the interior of the balloon 24 through an injection element 30, and a coolant recovery conduit 32 in communication with a vacuum source 34 for drawing expanded coolant from the interior of the balloon 24 to be vented to the atmosphere or stored in a coolant recovery reservoir 36. Additionally or alternatively, the balloon 24 may be in communication with another ablation energy source, such as a radiofrequency generator. The ablation device 12 may further include one or more sensors 37, such as temperature sensors, for monitoring the temperature and/or pressure of the balloon 24 and/or coolant delivery 26 and/or coolant recovery 32 conduits. Data recorded by the one or more sensors 37 may be communicated to the control unit 16 for communication to the operator and/or for the automatic or semi-automatic control of the system, for example, the temperature of the balloon 24.

The ablation device 12 may also include a shaft 38 or other actuator element in mechanical communication with one or more steering mechanisms in the handle 40 for navigating the device through the patient's vasculature to a target treatment site, such as proximate a pulmonary vein ostium within the left atrium of the heart. The shaft 38 may also be used to adjust the size and configuration of the balloon 24. For example, the shaft 38 may be slidingly and rotatably moveable within the elongate body 18, and a distal neck 42 of the balloon 24 may be coupled to a distal portion of the shaft 38. A proximal neck 44 of the balloon 24 may be coupled to the distal portion 22 of the elongate body 18. In this manner, longitudinal movement of the shaft 38 may alter the configuration of the balloon. For example, advancing the shaft 38 within the elongate body 18 toward the distal portion 22 may extend the balloon 24, causing the balloon 24 to transition into a more elongate configuration with a smaller outer diameter. Similarly, retraction of the shaft 38 within the elongate body 18 may cause the balloon 24 to transition to a shorter configuration with a larger outer diameter.

The shaft 38 may include a lumen through which a guidewire or mapping catheter 46 may be advanced through and to a location that is distal of the device 12. In a non-limiting example of an ablation procedure, the mapping catheter 46 may be advanced distally from the ablation device 12 and into a pulmonary vein. The distal portion of the mapping catheter 46 may be transitionable from an at least substantially linear configuration to an expanded configuration, such as a loop 48 shown in FIG. 2.

The second thermal treatment device 14, such as a cooling device. The cooling device 14 may also include an elongate body 50 having a proximal portion 52, a distal portion 54, and one or more lumens therebetween. The cooling device may be in communication with a cooling energy source and adapted for use with any of a variety of cooling modalities, including cryocooling using refrigerant or thermoelectric cooling. If the cooling device 14 is used to cool tissue using cryoablation, the device 14 may include an expandable element, such as a balloon 56, coupled to the distal portion 54 of the elongate body 50. Further, the balloon 56 of the cooling device 14 may be coupled to the elongate body 50 and may be configurable like the balloon 24 of the ablation device 12, with a shaft or actuator element that is in communication with the cooling device handle 60. Alternatively, the cooling device 14 may not include an actuator element or shaft, and the balloon 56 may be simply attached to the distal portion 54 of the elongate body 50 at a balloon 56 proximal neck 58. Alternatively, the balloon 56 may be coupled to the elongate body 50 in any other suitable manner.

The cooling energy source may be a coolant source. In this case, the elongate body 50 may further include a coolant delivery conduit 62 for delivering coolant from a coolant source. For example, the balloon 56 may be in fluid communication with the same coolant source 28 as the ablation device 12, or a secondary source of coolant 63 may be used. Alternatively, the balloon 56 may be in communication with a source of cooled fluid that is not a cryogenic fluid. That is, the cooled fluid may not expand within the balloon 56 to produce a temperature reduction by the Joule-Thomson effect. For example, a liquid such as water, saline solution, alcohol, or other suitable heat-transport medium may be used that has been cooled to an appropriate temperature. The cooling device 14 may also include a coolant recovery conduit 64 in communication with a vacuum source or other pump (which may be the same or different vacuum source 34 that is in communication with the ablation device coolant recovery reservoir 36) for drawing expanded or warmed coolant from the interior of the balloon 56 to be vented to the atmosphere, re-cooled and recirculated, or stored in a coolant recovery reservoir (which may be the same or different coolant recovery reservoir 36 that is in communication with the ablation device 12).

The cooling device 14 may also include one or more sensors 66 that function like the sensors 37 of the ablation device 12. For example, the cooling device 14 may include one or more temperature sensors 37 within the balloon 56, on an outer surface of the balloon 56, within the coolant delivery conduit 62, within the coolant recovery conduit 64, and/or at any other location suitable for recording temperature and/or pressure data and communicating that data to the control unit 16.

The control unit 16 may generally include all system elements that are not a part of the ablation device 12 and the cooling device 14, whether or not those system elements are located within the control unit 16 itself. For example, the control unit 16 may include the coolant source 28 and the coolant recovery reservoir 36, even though these elements may be located outside of the control unit 16. The control unit 16 may also include the vacuum source 34, a first power source 74 that is in communication with the one or more electrodes 68 of the mapping catheter 46. If the ablation and/or cooling device 12, 14 includes a thermoelectric cooling element, control unit 16 may also include a second power source that is in communication with the thermoelectric cooling element.

The control unit 16 may also include one or more computers 78 that include one or more processors 80, which may receive signals from the one or more sensors 37, 66 and the electrodes 68 of the mapping catheter 46. The one or more processors 80 may cause the one or more computers 78 to display data to the operator on one or more displays 82. As a non-limiting example, the one or more displays 82 may communicate to the operator the temperature and/or pressure of the balloons 24, 56 and/or mapping data from the mapping catheter 46. The operator may then adjust system 10 parameters manually using one or more user input devices 84, or the system 10 may automatically or semi-automatically adjust system 10 parameters, such as the flow of coolant into the ablation device balloon 24 or the flow of coolant or cooling fluid into the cooling device balloon 56.

Figure 2:
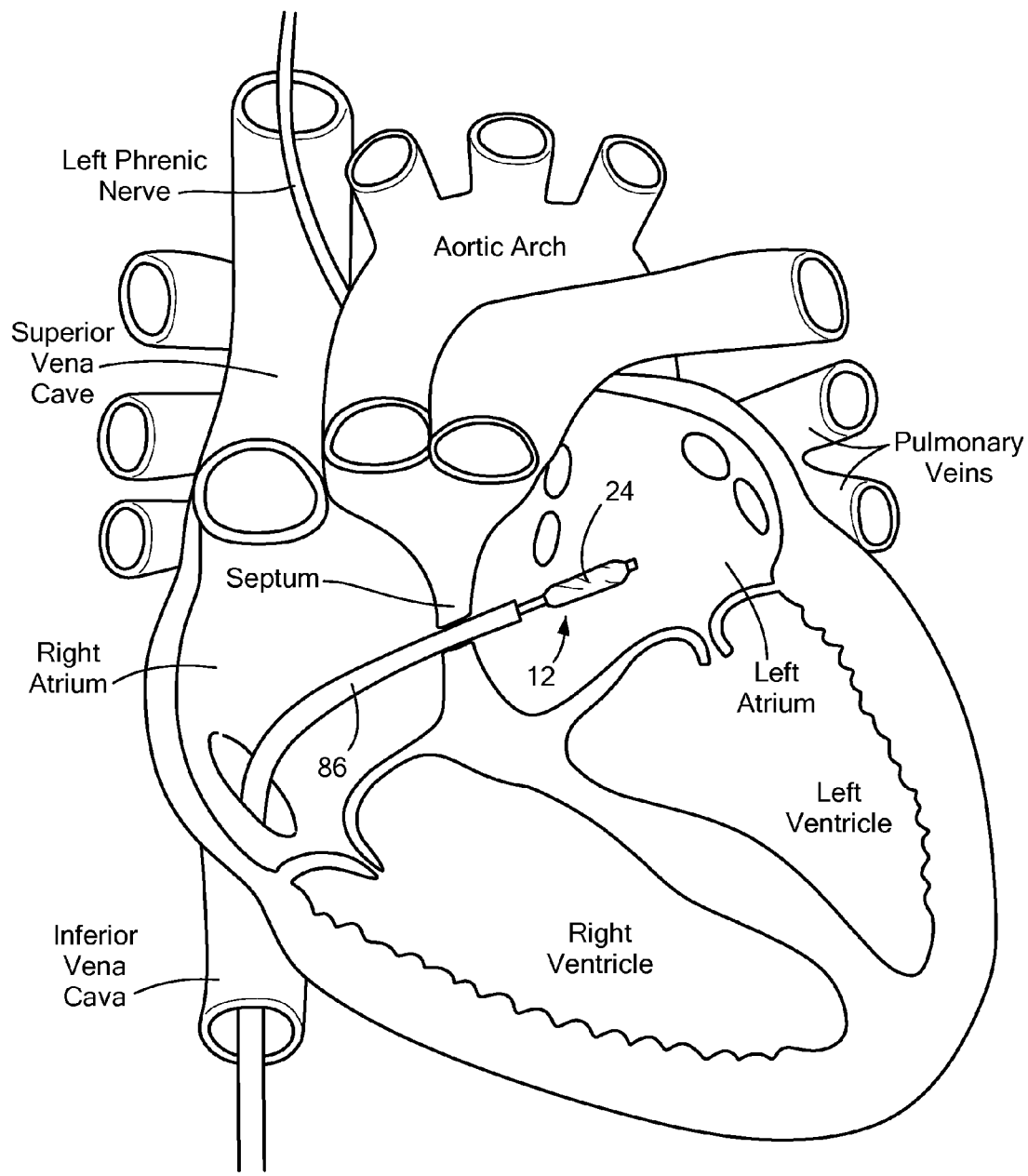
FIG. 2 shows a first step in a method for the treatment of cardiac arrhythmia in accordance with the present invention.
Figure 3:
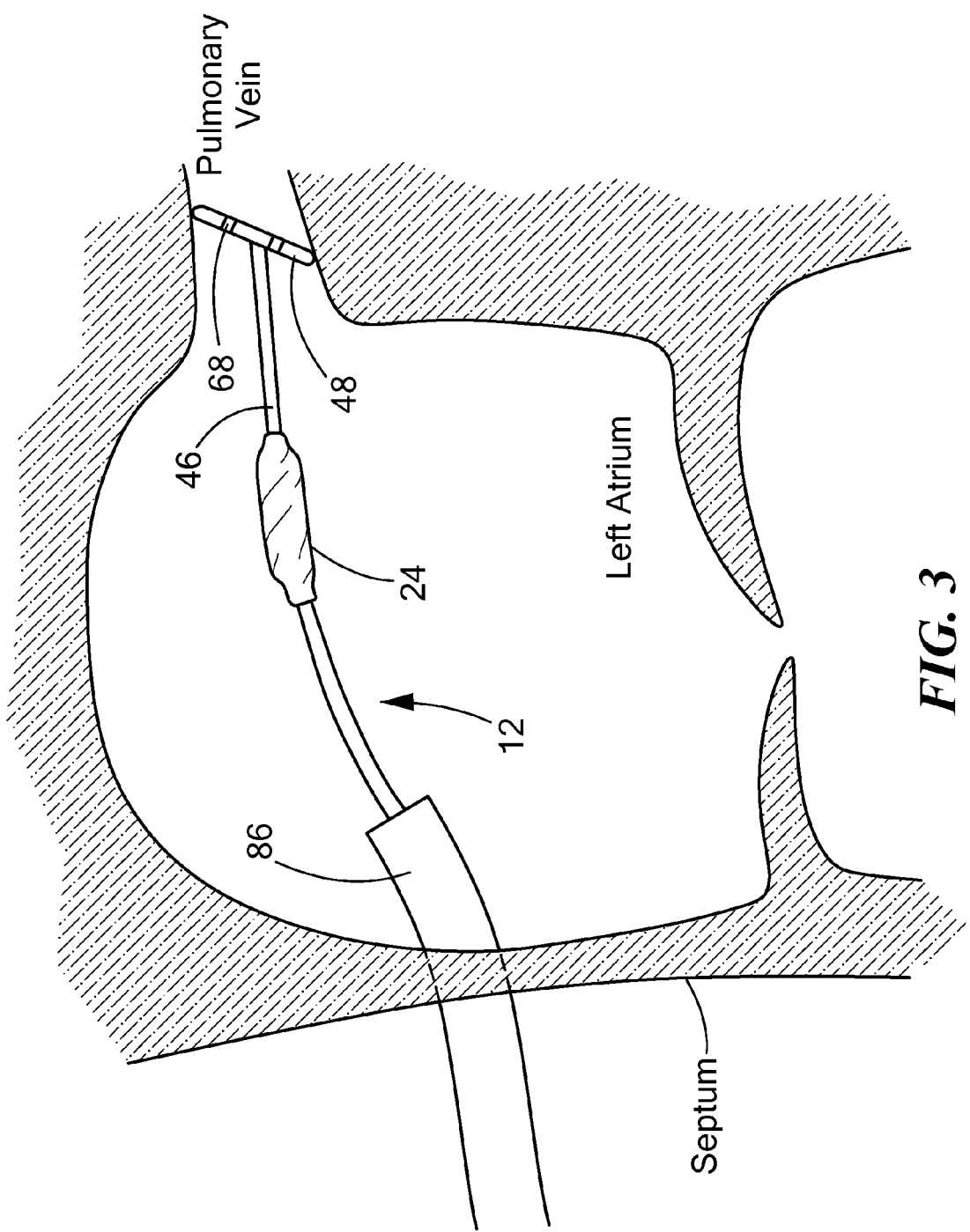
FIG. 3 shows a second step in a method for the treatment of cardiac arrhythmia in accordance with the present invention.
Figure 4:
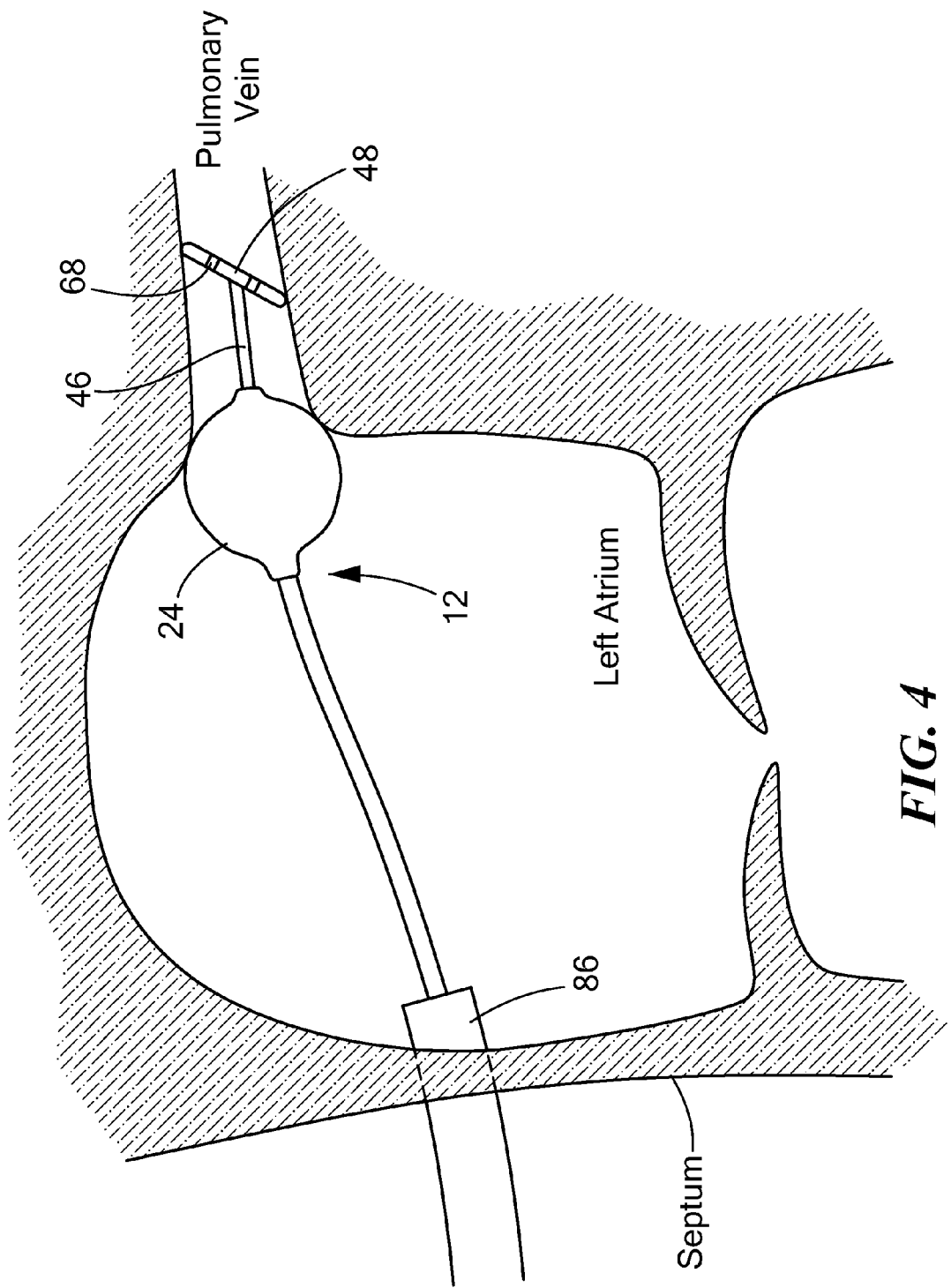
FIG. 4 shows a third step in a method for the treatment of cardiac arrhythmia in accordance with the present invention.

Referring now to FIGS. 2-4, a method for the treatment of atrial fibrillation is shown. As discussed above, the ablation device 12 may be navigated through the patient's vasculature to a target treatment site, such as the tissue proximate a pulmonary vein ostium, for an ablation procedure, such as a pulmonary vein isolation. As a non-limiting example, the ablation device 12 may be inserted into the patient's vasculature using femoral, brachial, or radial access. In the example shown in FIG. 2, the ablation device 12 may be inserted through the patient's femoral vein, through the inferior vena cava, and then into the right atrium. From the right atrium, the ablation device 12 may be advanced through the septum and into the left atrium (as shown in FIG. 2). As a non-limiting example, a septal puncture or opening for access to the left atrium may be created by a separate device before advancement of the ablation device 12. For example, a trans-septal device (not shown) may be advanced into the right atrium and used to create an opening within the septum for accessing the left atrium. A sheath or guide device 86 may be advanced over the device guidewire and through the septal opening to a location within the left atrium. The ablation device 12 may then be advanced through the sheath or guide device 86 and into the left atrium. Alternatively, the ablation device 12 may include one or more trans-septal elements (such as, for example, a needle or other piercing element) for creating the septal opening.

Once the ablation device 12 is located within the left atrium, the balloon 24 may be inflated by circulating coolant from the coolant source 28 within the balloon 24. Further, the mapping catheter 46 may be advanced through the ablation device 12 to a location distal of the ablation device 12. In the example shown in FIG. 3, the distal portion of the mapping catheter 46 may be transitioned from an at least substantially linear configuration to a loop configuration, and the loop 48 may be advanced to a location within a pulmonary vein such that at least a portion of the loop 48 is in contact with the inner surface of the pulmonary vein. The balloon 24 of the ablation device 12 may be inflated and advanced over the mapping catheter 46 until at least a portion of the balloon 24 is in contact with the tissue wall proximate the pulmonary vein ostium (as shown in FIG. 4). Mapping signals from within the pulmonary vein may be recorded by one or more electrodes 66 on the mapping catheter 46 and transmitted to the control unit 16 as discussed above.

Before, after, simultaneously with, or independent of the placement of the ablation device 12, the cooling device 14 may be positioned in the pericardial space. For example, the cooling device 14 may be inserted via subxiphoid access into the pericardial space (access shown in FIG. 5), passed beneath the ventricles, and positioned adjacent to the posterior wall of the left atrium (positioning shown in FIG. 6). The balloon 56 may be inflated once the cooling device 14 is at the target treatment location, such as by circulating coolant from the coolant source 28 or a secondary coolant source 63, or a cooling fluid from a secondary coolant source 63, within the balloon 56. Additionally or alternatively, mechanical means, such as pull wires, struts, pre-shaped elastic elements, shape-memory or super-elastic NiTi shaping elements, may be used to expand the balloon 56. The target location may be proximate the pulmonary vein having the arrhythmogenic source that is being treated by the ablation device 12. For example, the balloon 56 may be positioned between the posterior wall of the left atrium and the esophagus (as shown in FIG. 6). The cooling device 14 and the ablation device 12 may be activated simultaneously for at least a period of time, even if activation of one device is initiated before activation of the other device. Alternatively, the cooling device 14 and the ablation device 12 may be activated sequentially, or activation of both devices 12, 14 may be initiated simultaneously. The cooling device 14 may be activated (that is, a cryogenic or non-cryogenic fluid may be circulated within the balloon 56) to cause a reduction in temperature of tissue at the target location. For example, activation of the balloon 56 may cause a reduction in the temperature of adjacent pericardial tissue, such as pericardial adipose tissue, to a temperature of approximately 0° C. This tissue temperature may be maintained for a first time period to cause a reduction in adipose tissue over a second time period. For example, cooling adjacent adipose tissue for one or more periods of a few minutes, for example, between approximately two minutes and approximately ten minutes, may be used to cause a reduction in adipose tissue over a period of several weeks. As discussed above, cold-induced injury of the adipose tissue may lead to apoptosis and then phagocytosis.

Figure 5:
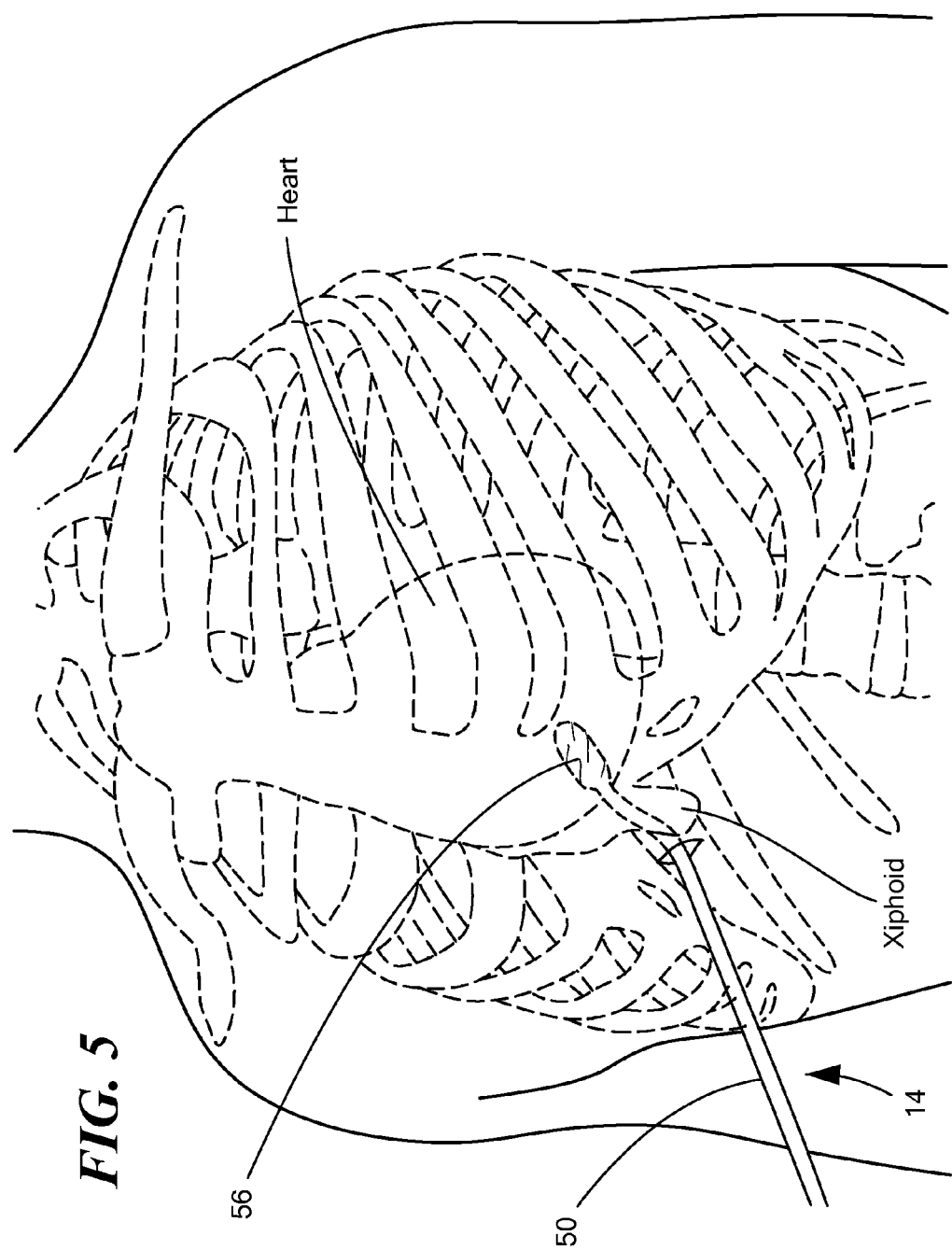
FIG. 5 shows a fourth step in a method for the treatment of cardiac arrhythmia in accordance with the present invention.
Figure 6:
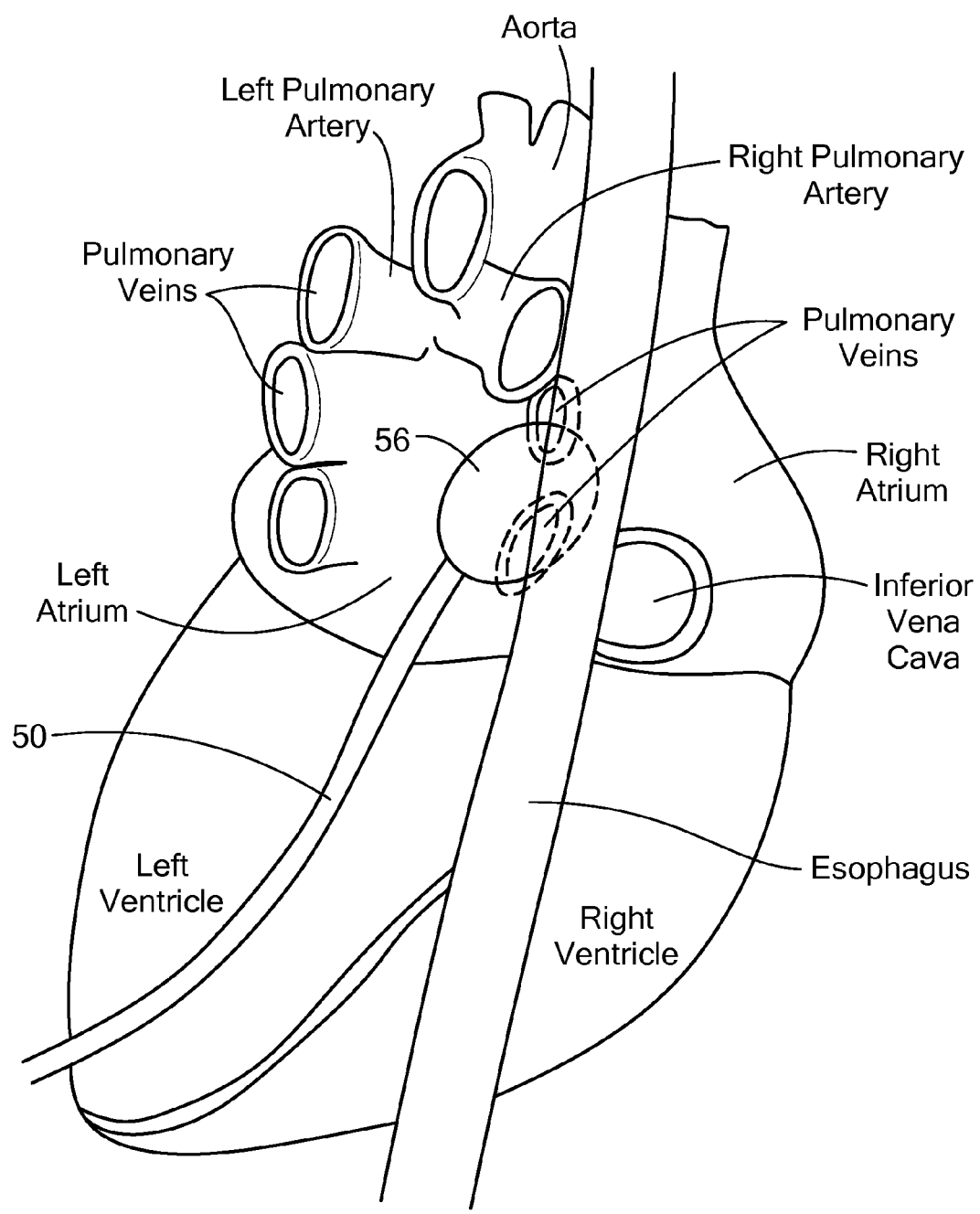
FIG. 6 shows a fifth step in a method for the treatment of cardiac arrhythmia in accordance with the present invention.

Although FIGS. 5 and 6 show subxiphoid access to the pericardial space, other minimally invasive access techniques may also be used. Further, although the cooling device 14 may be used to cool pericardial adipose tissue, room-temperature fluid may alternatively be circulated through the balloon 56. This fluid would not cause cryolipolysis, but may protect collateral structures from unintended damage by the ablation procedure. For example, positioning the cooling device 14 as shown in FIG. 6 may protect the esophagus from thermal damage caused by the pulmonary vein isolate procedure within the left atrium.

Figure 7:
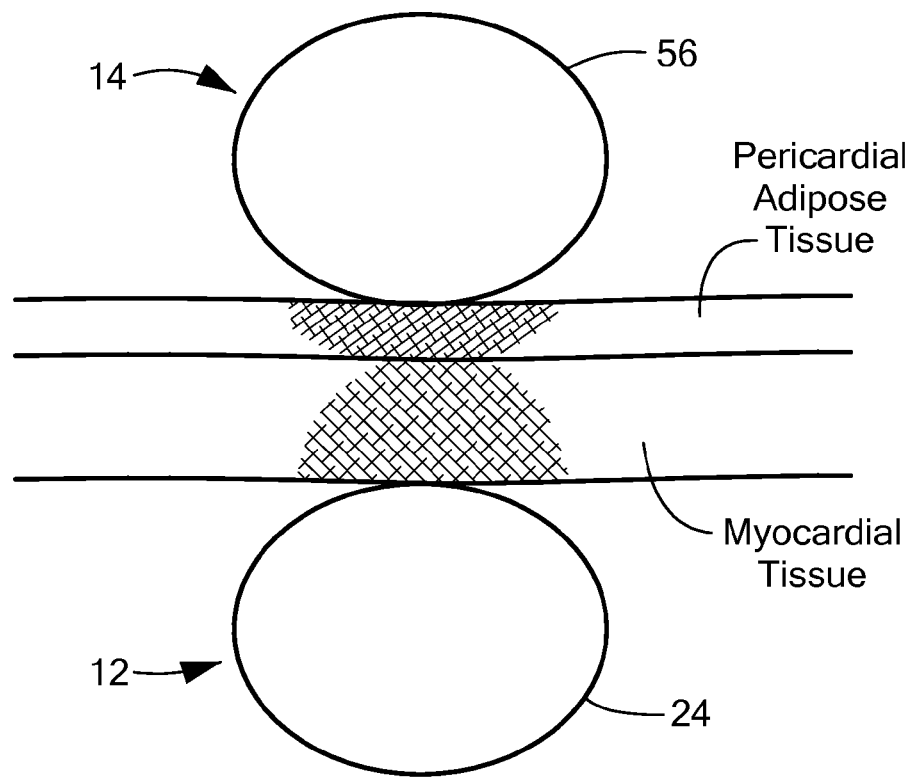
FIG. 7 shows a close-up view of cryolipolysis of pericardial adipose tissue and simultaneous cryoablation of myocardial tissue.
Figure 8:
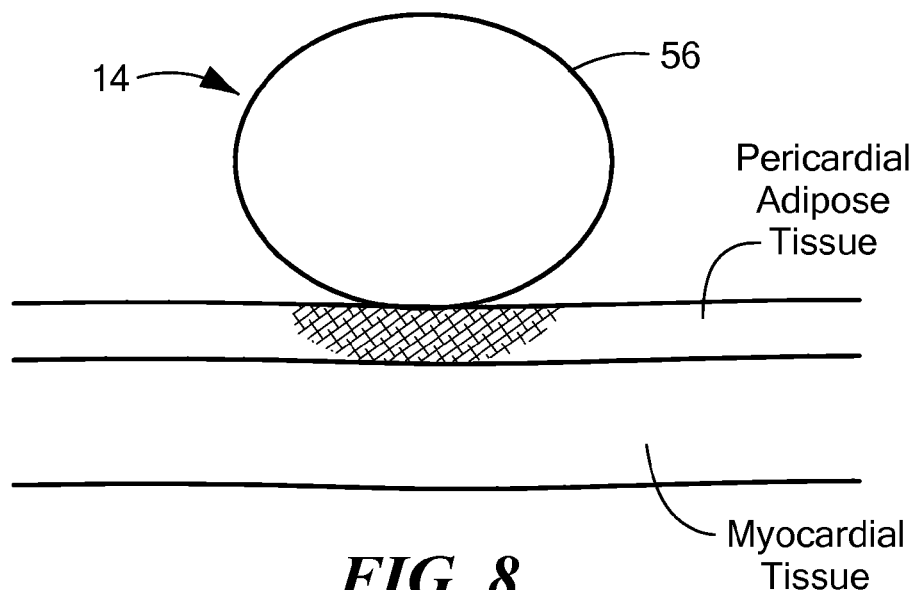
FIG. 8 shows a close-up view of cryolipolysis of pericardial adipose tissue without simultaneous cryoablation of myocardial tissue.

Referring now to FIG. 7, a close-up view of cryolipolysis of pericardial adipose tissue and simultaneous cryoablation of myocardial tissue is shown. The ablation device 12 may be positioned within the left atrium and in contact with tissue proximate a pulmonary vein ostium, as shown and described in FIGS. 2-4. When the ablation device 12 is activated (that is, when coolant is circulated within the balloon 24), adjacent myocardial tissue may become ablated. An exemplary ablation lesion is depicted with the x-shaped hash marks. The cooling device 14 may be positioned adjacent to the posterior wall of the left atrium, proximate the pulmonary vein being treated by the ablation device 12. When the cooling device 14 is activated (that is, when coolant or cooling fluid is circulated within the balloon 56), adjacent tissue may become cooled. For example, adjacent pericardial adipose tissue may become cooled to a temperature that causes adipose cell apoptosis. The area of cryolipolysis is depicted with slanted hash marks. Alternatively, cryolipolysis may be performed with the cooling device 14, as shown and described in FIG. 7, without the simultaneous cryoablation of myocardial tissue (as shown in FIG. 8). Performing cryolipolysis may provide a way of reducing pro-inflammatory cytokines, such as those pro-inflammatory cytokines released by pericardial adipose tissue proximate myocardial tissue, and thus reducing chronic inflammation of the myocardium. Further, as chronic inflammation may increase the likelihood of developing or increase the severity of atrial fibrillation, performing cryolipolysis may provide a way of treating atrial fibrillation.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A system for treating cardiac arrhythmia, the system comprising:
   a first thermal treatment device configured for placement within a mammalian heart in contact with myocardial tissue;
   a second thermal treatment device configured for placement in contact with pericardial tissue;
   a first energy source in communication with the first thermal treatment device, the first energy source causing the first thermal treatment device to reach a first temperature sufficient to ablate myocardial tissue when the system is in use;
   a second energy source in communication with the second thermal treatment device, the second energy source causing the second thermal treatment device to reach a second temperature that is sufficient for cryoliposis of adipose tissue but insufficient to ablate the myocardial tissue when the system is in use; and
   concurrent operation of the first energy source and the second energy source causing the first thermal treatment device to reach the first temperature and the second thermal treatment device to reach the second temperature when the system is in use.

2. The system of claim 1, wherein the first thermal treatment device is an ablation device.

3. The system of claim 2, wherein the first thermal treatment device is a cryoablation device including an elongate body and a cryoballoon coupled to a distal portion of the elongate body.

4. The system of claim 3, wherein the cryoballoon is in fluid communication with the first energy source.

5. The system of claim 4, wherein the first energy source is a coolant source containing a cryogenic fluid.

6. The system of claim 5, wherein cryogenic fluid is circulated within the cryoballoon when the cryoablation device is activated, activation of the cryoablation device causing the cryoballoon to ablate adjacent myocardial tissue.

7. The system of claim 1, wherein the second thermal treatment device is a cooling device including an elongate body and a balloon coupled to a distal portion of the elongate body.

8. The system of claim 7, wherein the second energy source is a coolant source containing at least one of a cryogenic fluid and a non-cryogenic fluid.

9. The system of claim 8, wherein at least one of the cryogenic fluid and the non-cryogenic fluid is circulated within the balloon of the cooling device when the cooling device is activated, activation of the cooling device causing the balloon to cause cryolipolysis of adjacent pericardial tissue for at least one period of time.

10. The system of claim 9, wherein the adjacent pericardial tissue is pericardial adipose tissue.

11. The system of claim 9, wherein activation of the cooling device causes a reduction in a temperature of adjacent pericardial tissue to approximately 0° C.

12. The system of claim 11, wherein the cooling device is configured to reduce the temperature of the adjacent pericardial tissue to approximately 0° C. for each of the at least one periods of time, each of the at least one period of time being between approximately two minutes and approximately five minutes.

13. A system for treating cardiac arrhythmia, the system comprising:
- an ablation device including an elongate body and an ablation element coupled to the elongate body, the ablation device being configured for placement within a mammalian heart in contact with myocardial tissue;
- a cooling device including an elongate body and a cooling element coupled to the elongate body, the cooling device being configured for placement in a pericardial space in contact with pericardial adipose tissue proximate the ablation element;
- an first energy source in communication with the ablation element, the first energy source causing the ablation element to reach a first temperature that is sufficient for myocardial ablation when the ablation element is activated;
- a second energy source in communication with the cooling element, the second energy source causing the cooling element to reach a second temperature that is sufficient for cryoliposis of adipose tissue but insufficient for myocardial ablation when the cooling element is activated;
- concurrent operation of the first energy source and the second energy source causing the first thermal treatment device to reach the first temperature and the second thermal treatment device to reach the second temperature when the system is in use.

14. The system of claim 13, wherein activation of the cooling element causes a reduction in temperature of adjacent pericardial adipose tissue to approximately 0° C.

15. The system of claim 14, wherein the temperature of the pericardial adipose tissue is reduced for at least one period of time, each of the at least one period of time being between approximately two minutes and approximately five minutes.

16. The system of claim 14, wherein the cooling element is configured to reduce pericardial adipose tissue over a first period of time when the cooling element is activated for a second period of time.

17. The system of claim 16, wherein the first period of time is greater than the second period of time.

18. A method for treating cardiac arrhythmia, the method comprising:
- positioning a cooling element at a first location within a pericardial space surrounding a heart of a patient, adjacent pericardial adipose tissue within the pericardial space;
- positioning an ablation element within the heart in contact with myocardial tissue at a second location proximate the first location;
- activating the cooling element to reduce the temperature of adjacent pericardial adipose tissue to approximately 0° C.; and
- activating the ablation element to ablate the myocardial tissue during at least a portion of a period of time during which the cooling element is activated.

19. The method of claim 18, wherein the temperature of the adjacent pericardial adipose tissue is reduced to approximately 0° C. for a first period of time and the temperature reduction causes a removal of the pericardial adipose tissue over a second period of time, the second period of time being greater than the first period of time.

20. The method of claim 18, wherein the cooling element and the ablation element are activated at different times.

21. The method of claim 20, wherein the ablation element and the cooling element are activated simultaneously.

22. The method of claim 20, wherein the cooling element is in communication with a source of cooling energy and the ablation element is in communication with a source of ablation energy.

23. The method of claim 22, wherein the source of cooling energy and the source of ablation energy are the same.

24. The method of claim 22, wherein the source of cooling energy is different than the source of ablation energy.

25. The method of claim 24, wherein the source of cooling energy is a non-cryogenic fluid and the source of ablation energy is a cryogenic fluid.

\* \* \* \* \*